US00PP09115P

United States Patent [19]

Kordes

[11] Patent Number: Plant 9,115

[45] Date of Patent: Apr. 25, 1995

[54] SHRUB ROSE PLANT NAMED 'KORTEMMA'

[75] Inventor: Wilhelm Kordes, Sparrieshoop, Germany

[73] Assignee: Bear Creek Gardens, Inc., Medford, Oreg.

[21] Appl. No.: 201,241

[22] Filed: Feb. 24, 1994

[51] Int. Cl.[6] ..... A01H 5/00
[52] U.S. Cl. ..... Plt./1
[58] Field of Search ..... Plt. 1, 28, 29

[56] References Cited

PUBLICATIONS

Dialog data base printout, Trademarkscan–Benelux–File 658, citation for 'Kortemma'.

*Primary Examiner*—Howard J. Locker
*Attorney, Agent, or Firm*—Klarquist Sparkman Campbell Leigh & Whinston

[57] ABSTRACT

Rose plant of the shrub class having bright red flowers; disease-resistant foliage; low-growing, spreading habit of growth; glossy, dark green foliage; and repeat flowering.

1 Drawing Sheet

1

The present invention relates to a new and distinct variety of rose plant of the shrub class which was originated by me by crossing the variety KORgram (unpatented) with the variety Walzertraum (unpatented).

The primary objective of this breeding was to produce a new rose variety having the spreading growth habit and disease-resistant foliage of the female parent combined with the bright red flower color and repeat flowering of the male parent. The objective was substantially achieved, along with other desirable improvements, as evidenced by the following unique combination of characteristics that are outstanding in the new variety and that distinguish it from its parents, as well as from all other varieties of which I am aware:

1. A spreading habit of growth;
2. Dark green, glossy, disease-resistant foliage;
3. Bright red flower color; and
4. Repeat flowering.

Asexual reproduction of this new variety by budding and by softwood cuttings, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Korgram.

*Pollen parent.*—Walzertraum.

Classification:

*Botanical.*—*Rosa hybrida.*

*Commercial.*—Shrub.

2

FLOWER

Observations made from specimens grown in a garden environment in Somis, Calif., and in Sparrieshoop, Germany.

Blooming habit: Recurrent.

Bud:

*Size.*—19 mm in length when the petals start to unfurl.

*Form.*—Short, pointed ovoid.

*Color.*—When sepals first divide, bud color is Red Group 46A. When half blown, the upper sides of the petals are Red Group 46B, and the lower sides of the petals are Red Group 53D.

*Sepals.*—Color: Green Group 139C. Surface texture: Covered in fine hairs and an occasional gland. There are three lightly appendaged sepals. There are two unappendaged sepals with hairy edges and glands on the edges.

*Receptacle.*—Color: Green Group 137D. Shape: Apple. Size: Small (6 mm×9 mm). Surface: Smooth with glands on lower portion of the receptacle.

*Peduncle.*—Length: Short (3.8 cm). Surface: Glandular. Color: Green Group 137D except where exposed to bright sun. It then becomes Bronzy. Strength: Stiff, erect, slender.

Bloom:

*Size.*—Small. Average open size is 7.6 mm in diameter.

*Borne.*—Several together in rounded clusters of from 3 to 7 blooms.

*Stems.*—Short (20 cm to 30 cm) and strong.

*Form.*—When first open: Cupped. Permanence: Flattens; outer petal edges curl slightly.

*Petalage.*—Number of petals under normal conditions: 20.

*Color.*—The upper side of the petals are Red Group 46B. The reverse side of the petals are Red Group 53D. The base of the petals has a small, greenish white half moon at the point of attachment (9 mm×9 mm). The major color on the upper side is Red Group 46B.

*Variegations.*—Occasional white streaks or spots occur on petals.

*Discoloration.*—The general tonality at the end of the first and third days: No change.

*Fragrance.*—Slight.

Petals:

*Texture.*—Thick.

*Shape.*—Deltoid.

*Form.*—Tips slightly recurved.

*Arrangement.*—Imbricated, with few petaloids in the center.

*Persistence.*—Drop off cleanly.

*Lastingness.*—On the plant: 5 days. As a cut flower: Not tested.

Reproductive parts:

*Anthers.*—Size: Medium. Quantity: Many. Color: White. Arrangement: Regular around the styles.

*Filaments.*—Color: Yellow.

*Pollen.*—Color: Gold Yellow.

*Styles.*—Color: Greenish white.

*Stigmas.*—Color: Greenish white.

Form: Shrub.

Growth: Vigorous, sprawling, compact. At one year of age, plant is 60 cm to 76 cm tall and 91 cm to 100 cm wide.

Foliage: Number of leaflets on normal mid-stem leaves: 5 or 7.

*Size.*—Medium (10 cm×6 cm).

*Quantity.*—Abundant.

*Color.*—New foliage: Reddish (Greyed Purple Group 183A), changing to dark green very quickly. Old foliage: Top surface, dark green (Green Group 135A). Undersurface, Green Group 137C.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Short (13 mm) serrated and bearded.

*Disease resistance.*—Resistant to mildew and rust under normal growing conditions at Somis, Calif., and Sparrieshoop, Germany.

Wood:

*New wood.*—Color: Light green. Bark: Smooth.

*Old wood.*—Color: Green. Bark; Smooth. Bark:

Prickles:

*Quantity.*—Ordinary on main canes from base and on laterals from main canes.

*Form.*—Short (6 mm), hooked downward.

*Color when young.*—Red.

Small prickles:

*Quantity.*—None on main stalks and laterals.

I claim:

1. A new and distinct variety of rose plant of the shrub class, substantially as herein shown and described, characterized particularly as to novelty by its bright red flowers; disease-resistant foliage; low-growing, spreading habit of growth; glossy, dark green foliage; and repeat flowering.

* * * * *

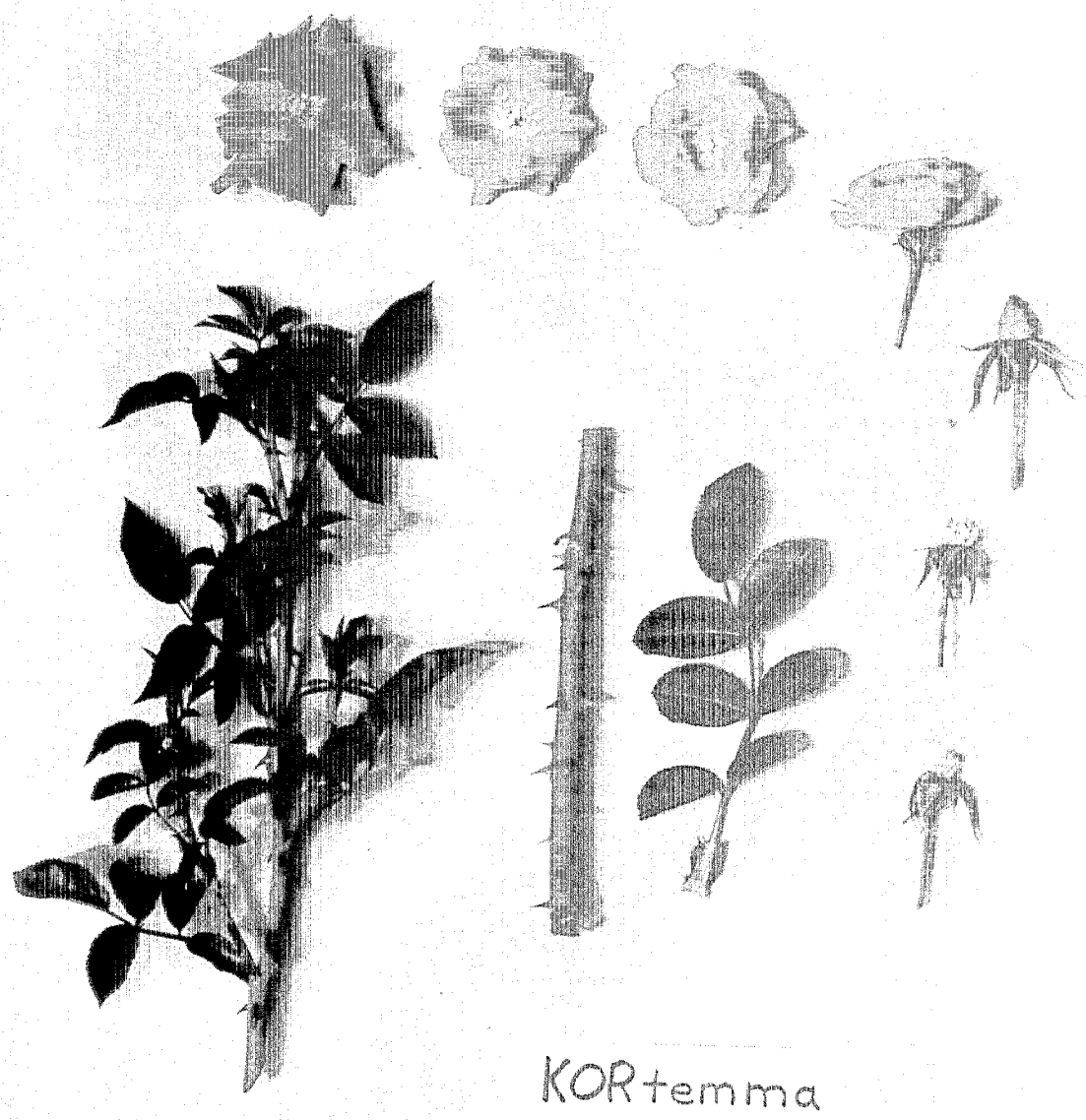
KORtemma

UNITED STATES PATENT AND TRADEMARK OFFICE

CERTIFICATE OF CORRECTION

PATENT NO. : PP 9,115

DATED : April 25, 1995

INVENTOR(S) : Wilhelm Kordes

It is certified that error appears in the above-identified patent and that said Letters Patent is hereby corrected as shown below:

Column 1, line 41, "Korgram" should read --KORgram--.

Signed and Sealed this

Eighth Day of August, 1995

*Attest:*

*Attesting Officer*

BRUCE LEHMAN

*Commissioner of Patents and Trademarks*